United States Patent [19]
Blackburn et al.

[11] Patent Number: 5,762,948
[45] Date of Patent: Jun. 9, 1998

[54] MOIST BACTERIOCIN DISINFECTANT WIPES AND METHODS OF USING THE SAME

[75] Inventors: Peter Blackburn; Jon de la Harpe, both of New York, N.Y.

[73] Assignee: AMBI Inc., Tarrytown, N.Y.

[21] Appl. No.: 479,280

[22] Filed: Jun. 7, 1995

[51] Int. Cl.⁶ .................................................. A61K 9/70
[52] U.S. Cl. ................................... 424/404; 424/402
[58] Field of Search .............................. 424/118, 120, 424/121, 404, 402; 514/2, 12

[56] References Cited

U.S. PATENT DOCUMENTS

| | | | |
|---|---|---|---|
| 2,830,011 | 4/1958 | Parker | 424/404 |
| 4,206,529 | 6/1980 | Neuman | |
| 4,253,420 | 3/1981 | Hoefelmayr | |
| 4,775,582 | 10/1988 | Abba et al. | |
| 4,853,281 | 8/1989 | Win et al. | |
| 5,124,145 | 6/1992 | Sordillo et al. | |
| 5,135,910 | 8/1992 | Blackburn et al. | |
| 5,139,788 | 8/1992 | Schmidt | |
| 5,217,950 | 6/1993 | Blackburn et al. | 424/118 |
| 5,234,684 | 8/1993 | Sordillo et al. | |
| 5,260,271 | 11/1993 | Blackburn et al. | |
| 5,304,540 | 4/1994 | Blackburn et al. | |
| 5,334,582 | 8/1994 | Blackburn et al. | |
| 5,366,732 | 11/1994 | Zighelboim | |

FOREIGN PATENT DOCUMENTS 0474506  11/1992  Japan ......................................... 424/404

OTHER PUBLICATIONS

Berg, et al., *J. Dairy Sci.*, vol. 68, pp. 457–461 (1985).
Pankey, et al., *Veterinary Clinics of North America*, vol. 9, pp. 519–530 (1993).
McKinnon, et al., *J. of Dairy Research*, vol. 50, 153–162 (1983).
Murdough, et al., *J. Dairy Sci.*, vol. 76, pp. 2033–2038 (1993).
Ansari, et al., *Am. J. of Infection Control*, vol. 19, pp. 243–249 (1991).

*Primary Examiner*—Thurman K. Page
*Assistant Examiner*—Kathryne E. Shelborne
*Attorney, Agent, or Firm*—White & Case

[57] ABSTRACT

Disclosed are novel, moist paper or fabric wipes containing a bacteriocin disinfectant formulation, which have a low alcohol content and which afford rapid, one-step disinfection and drying of surfaces. Also disclosed is a method of disinfection and drying of skin, including cow teat skin, either prior to or after milking, which employs the wipes.

20 Claims, No Drawings

1

MOIST BACTERIOCIN DISINFECTANT WIPES AND METHODS OF USING THE SAME

BACKGROUND OF THE INVENTION

Moist disinfectant wipes or towelettes are currently available commercially and are produced in a variety of forms. The wipes currently available have a number of uses including the disinfection of hands, skin, food lines and hospital surfaces, as well as applications in the dairy industry.

Moist disinfectant wipes presently available typically contain a germicide such as chlorhexidine, chlorhexidine digluconate or povidone-iodine and/or an alcohol as the disinfecting agent(s). The alcohol component, generally in a concentration of 70% or greater, also serves as a drying agent. While efficient drying of a surface exposed to a moist wipe is important, the high concentration of alcohol commonly used poses a problem of excess drying and chapping of skin. There is a further concern with the flashpoint of formulations with such a high alcohol content. Furthermore, the disinfectants commonly used are not of ideal potency, and the amounts required to obtain reasonable disinfection properties can present toxicity or sensitization problems.

One particular area wherein the problems have not been completely addressed by the disinfecting methods currently known is the dairy industry. The dairy industry incurs tremendous losses, upwards of 2 billion dollars per year in the United States alone as a result of mastitis. The practice of appropriate udder hygiene prior to, during, and after milking is recommended in order to control mastitis infection.

Preparation of a dairy cow for milking is viewed as the most labor intensive and time consuming part of the milking procedure. Commonly, dairy farmers use one of two different methods. The most prevalent method is udder washing. This practice consists of using an udder wash solution, individual paper towels and water. The udder wash solution may be injected into the stream in a water hose and sprayed onto the udder. Alternatively a towel is soaked in the udder wash solution in a bucket and the damp paper towel is used to wash and massage the udder. In each case the udder is then dried with a paper towel.

Predipping with a germicidal teat dip has replaced udder washing in approximately 40% of the U.S. dairy farms. The herdsman will dip or spray the cows' teats (as opposed to the complete udder) with a teat dip, allowing the dip to stay in contact with the teat for at least 15 seconds. The teat dip solution is then wiped off with a paper towel.

While each of these methods has certain advantages, neither effectively addresses all of the concerns encountered in this milieu. Among the concerns are effective cleaning and drying, contamination of milk by udderwash runoff and/or predip residues, and efficient use of labor and time in preparing the cow.

Much effort has been put into remedying the widespread and costly bacterial contamination of milk. Various improved methods for pre-milking treatment of udders and methods for the prevention and treatment of bovine mastitis have been described (see, e.g., U.S. Pat. No. 4,206,529 to Neumann; U.S. Pat. Nos. 5,124,145 and 5,234,684 to Sordillo, et al.; U.S. Pat. No. 4,253,420 to Hoefelmayr and U.S. Pat. No. 5,366,732 to Zighelboim). Others have described improved antimicrobial compositions which have particular application to the problem of contaminating residues in premilking sanitizing operations (see, e.g., U.S. Pat. No. 5,139,788 to Schmidt) or have described improved systems of general applicability for delivery of moist wipes (see, e.g., U.S. Pat. No. 4,775,582 to Abba, et al. and U.S. Pat. No. 4,853,281 to Win, et al.). Berg, et al., *J. Dairy Sci.* 68, 457–461 (1985); Pankey, et al. *Veterinary Clinics of North America* 9, 519–530, 1993; McKinnon, et al., *J. Dairy Res.* 50, 153–162, 1983; Murdough, et al., *J. Dairy Sci.* 76, 2033–2038, 1993 and Ansari, et al., *Am. J. Infect. Control* 19, 243–249, 1991 provide further description of the present state of the art and describe the evolution of udder hygiene in terms of various aspects of the commonly applied procedures for pre-milking sanitization of teats.

There is thus a need for moist disinfectant wipes which provide efficient one-step disinfection and drying of surfaces but which employ disinfecting agents with greater bactericidal potency yet fewer possible undesirable side effects. The improved wipes should also provide efficient drying without chapping or other loss of integrity of sensitive surfaces.

SUMMARY OF THEE INVENTION

The present invention concerns novel, moist paper or fabric wipes which afford rapid, one-step disinfection and drying of surfaces. The wipes contain a liquid disinfectant formulation typically comprising a bacteriocin as the disinfecting agent, a stabilizer for the bacteriocin, a chelating agent, a surfactant, a salt, a skin conditioner or humectant, and an agent to promote rapid drying. The bacteriocin disinfecting agent can also be combined with commonly used germicidal agents, as appropriate. In the wipes of the present invention, said germicidal agents can be employed in much lower amounts, thus alleviating toxicity and sensitization concerns. Because the inventive wipes employ bacteriocins, i.e., far more potent bactericidal agents, the alcohol component is required primarily as a drying agent, and thus the required concentration of alcohol is substantially lowered relative to that required for bactericidal action. This provides a remedy for the typically encountered problem of chapping of sensitive surfaces by high-alcohol formulations.

The wipes of the instant invention are suited to disinfection and drying of any surface where sanitization is required. One particular application of the inventive wipes is the rapid and efficient disinfection and drying of cow teats. The present invention further concerns a method of reducing the incidence of mastitis infection in dairy animals which employs the novel wipes.

U.S. Pat. Nos. 5,135,910; 5,217,950; 5,260,271; 5,304,540 and 5,334,582 all disclose broad range bactericidal compositions comprising a lanthocin (a lanthionine-containing bacteriocin) such as nisin, and a chelating agent. The patents further disclose a number of uses for the compositions based on their bactericidal properties. Consept, a nisin-containing formulation within the scope of the compositions disclosed in the cited patents, has been on the market for a number of years. The wipes of the instant invention typically contain formulations such as those disclosed in the above-cited patents, which are incorporated herein by reference.

DETAILED DESCRIPTION OF THE INVENTION

The instant invention provides a disposable wipe of a paper or cloth fabric typically with a bacteriocin-based formulation further comprising a chelating agent, a salt component, a stabilizer, a drying agent and a surfactant. The wipes of the instant invention provide efficient one-step disinfection and drying of surfaces and have applicability to any situation requiring sanitization of a surface. One particular application is in the disinfection and drying of cow teats.

The wipes of the instant invention contain a disinfectant formulation typically comprising as active ingredient a bacteriocin in combination with a salt component. The preferred active agent is a lanthocin (a lanthionine-containing bacteriocin) such as nisin, subtilin, epidermin, gallidermin, cinnamycin, duramycin, ancovenin or Pep 5. Other peptide bacteriocins such as lysostaphin may also suitably be employed. The bacteriocin agents of the instant invention are much more potent than commonly used germicides and do not exhibit undesirable side effects. The active agents of the formulations according to the instant invention are not confined, however, to peptide bacteriocins; other antibacterial agents such as chlorhexidine may suitably be employed in combination with the bacteriocins of the invention. The presence of the bacteriocin component allows the employment of the chlorhexidine or other non-bacteriocin germicidal component in much lower concentrations, thus eliminating concerns regarding unwanted side effects. Furthermore, the active agent may comprise two or more bacteriocins in combination or a bacteriocin in combination with another antibacterial agent. The most preferred embodiment of the instant invention known at this time comprises nisin as active ingredient.

The use of bacteriocins such as nisin in conjunction with a paper or cloth wipe has inherent difficulties due to the peptide nature of the active ingredient. It would be expected that such compounds adsorbed onto a wipe would not easily be released from the wipe, in the instant case onto the site where disinfection is desired. Accordingly, the formulations of the instant invention further comprise a component to increase the ionic strength and which thus serves to loosen the links between the bactericidal agent and the surface of the wipe. This component has also been found to be a factor in enhancing the stability of the active agent while in contact with the wipe. Suitable agents for increasing the ionic strength are halide salts of carboxylates, hydroxyacid salts, salicylates, glycolates, phosphates and polyphosphates. A preferred component is NaCl in a concentration range of 10 to 100 mM. The preferred concentration of NaCl is 50 mM. Another preferred component is sodium citrate in a concentration range of 1 to 10 mM. The preferred concentration of citrate is 5 mM.

It has been found (see U.S. Pat. Nos. 5,135,910; 5,217, 950; pending U.S. application Ser. No. 08/386,122 incorporated herein by reference) U.S. Pat. Nos. 5,260,271; 5,304, 540 and 5,334,582, incorporated herein by reference) that lanthocins in combination with a chelating agent exhibit enhanced potency and broader range as bactericides. Accordingly, the formulations of the instant invention typically contain a chelator component. Suitable chelating agents are, for example, EDTA, CaEDTA, CaNa$_2$EDTA and other alkyldiamine tetraacetates, as well as EGTA and citrate. The preferred chelating agents are EDTA (1-10 mM) and/or citrate (1-30 mM). The most preferred concentrations of EDTA and citrate are 3 mM and 5 mM, respectively. The chelating agents may be used alone or in combination.

The preferred peptide bacteriocins of the instant invention are somewhat labile, and degradative losses can be incurred when the bacteriocin is in contact with the wipe. It has been found (pending U.S. application Ser. No. 08/386,122, incorporated herein by reference) that methionine and related thioether compounds act to protect bacteriocins, particularly nisin, against degradation. Accordingly, methionine is typically a component of the formulations of the instant invention. Methionine is employed in a concentration range of 1–10 mM, the most preferred concentration being 2 mM. A combination of EDTA and citrate has also been found not only to impart the properties described above for chelators, but additionally to enhance the stability of the bacteriocin component.

Also along the lines of stabilization of the active agent, catalase may be added to the formulation to destroy any peroxides which may be present. Catalase may typically be employed at a concentration range of 6 to 600 units/ml. The most preferred concentration of catalase is 60 units/ml.

Another important component of the formulation is a drying agent. A fine balance must be achieved between formulations which are too "wet" and ones which are too "dry." As described above, too much moisture during the disinfecting procedure can interfere with the disinfection process; enhance the chances of cross contamination; and, particularly in the case of sensitive surfaces such as skin and teats, cause irritation. On the other hand, a minimal amount of "wetness" must be maintained in order that the bacteriocin component function optimally; the wipes according to the instant invention are not "moisture activated," but a minimally moist environment must be maintained to assure the desired efficacy. Furthermore, formulations which promote too rapid or complete drying can promote irritation of sensitive surfaces. Accordingly, the formulations of the instant invention typically further comprise a drying agent such as an alcohol. Because of the bacteriocin component employed in the inventive wipes, the alcohol component is required only in the capacity of drying and not in that of disinfection. Therefore, the formulations of the instant invention contain far less alcohol than typically required in known wipe formulations. The typical concerns of surface sensitivity and flashpoint associated with high alcohol content are thus circumvented. Among the alcohols suitable for use in the inventive wipes are methanol, ethanol, 1-propanol, 2-propanol, and benzyl alcohol. The preferred drying component is 1-propanol in a concentration of 10 to 20% w/v. The most preferred concentration for 1-propanol is 12% w/v.

The patents cited above as directed to nisin-chelator compositions also disclose that a surfactant component may further enhance the potency and range of activity of lanthocin-containing bactericidal compositions. The formulations of the instant invention may further comprise such a component. Such components include nonionic and amphoteric surfactants and emulsifiers, quaternary compounds, monoglycerides and fatty acids. More particularly such components may be selected from among glycerol monolaurate (0.03 to 0.3% w/v); nonionic surfactants such as polysorbate 20 (0.1 to 3% w/v), Arlasolve 200 (0.1 to 3% w/v), and Triton X-100 (0.1 to 3% w/v); cationic agents such as lauramine oxide (0.1 to 3% w/v); or zwitterionic agents such as cocoamidopropyl betaines (0.1 to 3% w/v). The preferred surfactant component presently known is the nonionic surfactant polysorbate 20 at a concentration of 1% w/v.

The wipe formulation of the instant invention may further comprise a conditioner/humectant component and a thickening agent. The conditioner is particularly useful when the wipe is applied to easily irritated skin surfaces. Typically this component may be selected from propylene glycol, glycerol, sorbitol and lactylate each in the concentration range of 1 to 10% w/v. The preferred conditioner is propylene glycol at a concentration of 10% w/v. The thickening agent may be selected from hydroxyethyl cellulose, methyl cellulose, polyvinyl pyrrolidone or mixtures of these agents, each in the concentration range 0.1 to 1% w/v. Hydroxyethyl cellulose at 0.35% w/v is the preferred component according to the instant invention. The liquid-carrying capacity of the wipe may be increased when a thickener is a component of the wipe formulation.

The pH of the formulations is adjusted to the range from 3.0 to 5.0. The preferred final pH of the formulations is 3.5.

The '910, '950, '271, '540 and '582 patents cited above disclose a number of compositions and formulations which comprise various combinations of ingredients recited above in the description of the instant formulations. The patents are incorporated by reference for their disclosure of the production of nisin chelator compositions, compositions which may be used in the wipes of the instant invention.

The choice of paper wipe to be used in conjunction with the nisin-based formulation is also important to the successful carrying out of the invention. Some papers, for example, do not allow advantageous adsorption of the active agent. This could result either in insufficient adsorption of active ingredient by the wipe or difficulty in releasing the active ingredient from the wipe to the target area. Other considerations in this regard are cost, texture with respect to impact on skin, liquid capacity per towelette, liquid residue left on skin and tensile strength of the paper when wet. The best papers which are currently known to the inventors are hydroentangled cellulose.

According to the instant invention, the wipes may be dispensed by a variety of means, all of which are designed to preserve the integrity of unused wipes from soiling and to prevent premature drying of the wipes. The wipes may be dispensed from a center-pull dispenser via a roll, in a layered manner, an interfold/interleaved manner or a pop-up manner from a canister. Another aspect of the invention provides for the dispensing of wipes from a recyclable, disposable, sealed plastic bag.

The dispenser may take the form of a belt holster for the convenience of the user or mounted close at hand to each workstation. A "disposable bag"-type dispenser would be suitable for mounting throughout the area of use. One aspect of the invention deals with reusable dispensers, a concept which addresses the problem of waste disposal.

The packaged product may suitably take a number of forms, including a package prefilled with both towelette and liquid formulation, a canister containing dry towelettes with the liquid component to be added immediately prior to dispensing, a reusable canister to which towelettes and liquid may be added at the appropriate time, or a package containing dry towelettes impregnated with reagents to which water or formulated liquid components could be added at the appropriate time prior to use.

One application of the wipes of the present invention provides a method of pre-milking preparation of cows' teats, combining the advantages of udder washing (removal of excess soilage, mechanical stimulation of the udder to promote milk "let-down"); of pre-dipping with a germicide (sanitize the teat skin and teat end, remove excess residues and dry off with a paper towel); speed and economy of effort in one step. As dairies become larger and the practice of milking cows three times a day becomes more prevalent, so grows the importance of time-saving practices and means of increasing milking efficiency. The inventive disposable moist wipes and one-step procedure according to the instant invention address the primary concerns with regard to pre-milking preparation set forth by the National Mastitis Council (NMC) in its guidelines. The treatment according to the instant invention decreases the required time and labor for preparing the animals and increases milking efficiency. The practice of premilking hygiene promotes the reduction of bacterial contamination of milk which has been the focus of studies for many years and remains of prime importance.

Pre-milking treatment of the teats with the towelettes of the instant invention removes any debris or soilage from the milking-unit-contact-surface of the teat, stimulates the release of oxytocin by massage of the udder, thus enhancing milk "letdown," provides a germicidal action to kill mastitis-inducing bacteria on the teat, and leaves a minimum and quick drying residue of liquid on the teat, thus eliminating the need to dry the teat by a separate step.

The application of the disposable wipes according to the instant invention can likewise provide time and labor-saving benefits when used to clean and sanitize the skin during gloveless food handling (while minimizing the risk of contaminating the food with germicidal residues) The application of the instant invention would provide similar benefits when used to clean and sanitize food contact hard surfaces or other food contact inanimate surfaces. The application of the disposable wipes according to the instant invention can likewise provide time and labor-saving benefits when used to cleanse the skin of the head, neck and face, or any skin surface that may benefit from combined cleansing and sanitization with a moist wipe leaving behind a rapidly drying moist residue. the cleansing quality of the wipe can provide a fresh or cleansing benefit to the user. Likewise, the cleansing and germicidal qualities can be used before and after minor surgical procedures or prior to other procedures which may entail breaking the integrity of the skin, such as puncturing as encountered during application of a hypodermic needle.

The towelettes may be located in a stationary HDPE plastic container or alternatively in a belt-mounted dispenser that is strapped around the waist. The towelettes could be in the form of a center-pull roll in a cylindrical tub or interleaved in a rectangular container and soaked in the germicidal solution according to the instant invention. A dispenser with a pull-through mechanism would minimize the likelihood of soiling the stock of towelettes.

Employment of the towelettes of the instant invention has a number of advantages over currently employed procedures. Among these are that cleaning and sanitizing become a single operation, saving time and effort, and the operator's hand is simultaneously sanitized each time at the point of application. For the dairyman current procedures comprise separate steps of removing dirt, sanitization with teat dip, and drying with a paper towel; now a single product can accomplish all these steps. Furthermore, a single-use paper wipe eliminates cross-contamination. The disclosed treatment effectively addresses the NMC recommended practice of avoiding excess liquid from udderwashing running down the teat; minimal or no liquid residue remains on the teat and gets into the milk supply.

The wipes provide for optimal measured delivery of adequate germicidal agent and optimal drying of treated area. In addition the wiping action physically removes bacteria (>90%) as well as superficial debris and, when used with dairy cows, further provides for simultaneous stimulation of milk let-down by massaging action. The amount of sanitizer required is reduced due to elimination of the necessity for frequent discard of product from the teatdip cup, required to overcome/prevent crosscontamination by soiled germicidal solution in the cup.

The treatment according to the instant invention can also be used beneficially in a post-milking regimen. This aspect of treatment provides mechanical removal of residual milk from "open" teat orifice and concomitant reduction of likelihood of infection, as well as a "dry" teat protected from the risk of chapping and "freezing" in cold weather. The post-milking sanitization also affords an additional measure of prevention of mastitis.

EXAMPLE 1

To determine whether methionine could protect the nisin from degradation when the nisin is exposed to the paper towels, nisin-based sanitizer formulation (PDF) was prepared with methionine at concentrations from 0 to 100 mM. Fresh sections of paper towel were incubated in these solutions and samples of the PDF were analyzed for nisin content at intervals over 6 days. Nisin content was determined as absorbance at 210 nm after separation by HPLC. Methionine was seen to give protection against loss of nisin. Chromatograms of the samples showed degradation of the nisin into multiple components in the control samples without methionine and protection against this degradation in samples containing methionine.

| | |
|---|---|
| 1-propanol | 24 ml |
| propylene glycol | 6 ml |
| 10% polysorbate 20 | 6 ml |
| 100 mM EDTA | 1.2 ml |
| water | qs 60 ml |
| pH adjusted to 3.5 | |

| | Met (200 mM) | nisin (10 mg/ml) | PDF | $H_2O$ |
|---|---|---|---|---|
| 1. | 0 ml | 0.045 ml | 8.96 ml | 9.0 ml |
| 2. | 0.45 ml | 0.045 ml | 8.96 ml | 8.55 |
| 3. | 0.9 | 0.045 ml | 8.96 ml | 8.1 |
| 4. | 1.8 | 0.045 ml | 8.96 ml | 7.2 |
| 5. | 4.5 | 0.045 ml | 8.96 ml | 4.5 |
| 6. | 9.0 | 0.045 ml | 8.96 ml | 0 |

To 50 ml polypropylene tubes were added 100 cm$^2$ (10 cm×10 cm) pieces of paper towel and 9 ml aliquots of the given test solution. The tubes were then rocked gently at room temperature and 400 ul aliquots were taken at various times for nisin analysis. The data suggest that the presence of methionine protects against the loss of nisin by degradation. Studies on the stability of nisin exposed to the paper wipes also revealed loss of nisin without the corresponding appearance of degradation products. This loss suggested there was a further source of nisin instability in the moist wipes product and that methionine did not protect against this second form of loss.

EXAMPLE 2

Nisin in a wipes formulation is stabilized from degradation by methionine and from adsorptive loss by addition of salt.

The results indicate that the presence of sodium chloride reduces the adsorptive loss of nisin, and that methionine and sodium chloride together stabilize nisin in the wipes formulation and allow recovery of >90% of the nisin in the samples after 6 days at room temperature.

EXAMPLE 3

Nisin in a wipes formulation is stabilized from degradation by addition of methionine and from adsorptive loss by the addition of salt. Paper types from various sources encompassing a range of compositions, weights, feel and tensile strengths were evaluated for their suitability with the wipes formulation.

PDF (25 ug/ml nisin) was prepared as outlined in Table I. For each condition in the experiment, a 100 cm$^2$ section of towel was placed in a 50 ml conical polypropylene tube. 9 ml test solution was added, and the tubes were placed on a rocker table at room temperature. Samples of liquid (1ml) were withdrawn for analysis after 3 days (Table II).

The data shown in Table II confirm that nisin in the wipes formulation is stabilized by the addition of salt and methionine to the formulation. The data further illustrate that this permits a wide range of papers to be used, but that hydroentangled cellulose was the most suitable choice of paper.

TABLE I

PDF Formulations

| | A regular | B +Met | C +Met +NaCl |
|---|---|---|---|
| 1-propanol (%) | 20 | 20 | 20 |
| propylene glycol (%) | 10 | 10 | 10 |
| polysorbate 20 (%) | 1 | 1 | 1 |
| EDTA mM | 1 | 1 | 1 |
| methionine mM | — | 10 | 10 |
| NaCl mM | — | — | 100 |
| nisin ug/ml | 25 | 25 | 25 |
| DI water | qs | qs | qs |

TABLE II

Evaluation of towel samples for softness, strength, and residual nisin concentration in the liquid phase after 3 days at room temperature.

| | weight g/yd$^2$ | soft-ness* | strength** | control Nisin, g/ml | +Met | +Met +NaCl |
|---|---|---|---|---|---|---|
| polyester/cellulose | 57 | 4 | 4 | 0 | 4 | 28 |
| cotton 100% | | 3 | 1 | 7 | 12 | 23 |
| Rayon/polypropylene | 45 | 3 | 3 | 10 | 15 | 26 |
| Rayon acrylic | 45 | 4 | 3 | 9 | 17 | 25 |
| carded Rayon 100% | 26 | 4 | 2 | 0 | 3 | 20 |
| carded Rayon 100% | 32 | 4 | 2 | 0 | 0 | 12 |
| Rayon/cellulose wetlaid | 26 | 3 | 2 | 1 | 3 | 26 |
| paper crepe | 23#/R | 2 | 2 | 4 | 9 | 29 |
| control | | | | 26 | 27 | 27 |
| Rayon 70/30 | 30 | 4 | 3 | 6 | 10 | 19 |
| cellulose hydro-entangled | 31 | 3 | 3 | 22 | 26 | 28 |

*1 = harsh 4 = soft
**1 = tears easily 4 = resists tearing

EXAMPLE 4

The germicidal potency of wipes formulations was evaluated against bacterial suspensions of *E. coli* strain ATCC 8739 and *S. aureus* strain ATCC 6538. The formulation compositions were identical to that illustrated in Table I, but with 12% 1-propanol and with 10% propylene glycol substituted with 5% glycerol. In addition, a range of concentrations of benzyl alcohol and/or citrate were added to the formulations. Further, the test formulations were evaluated for germicidal potency in the presence of 50% by volume whole milk to act as an organic load. Formulations were preincubated 2 hours in the presence of milk, then their germicidal performance was evaluated after 1 minute incubation with bacteria suspensions at 37° C.

The data in Tables III and IV illustrate that addition of citrate enhances the germicidal potency of nisin-based formulation, particularly in the presence of the organic load provided by milk. The combination of the chelators, citrate and EDTA, in the formulation was surprisingly effective at overcoming divalent cations present in the milk. Also, the germicidal performance of the formulations was further improved by the incorporation of benzyl alcohol.

TABLE III

| | | E. coli (cfu/ml)* | |
|---|---|---|---|
| % benzyl alc | % citrate | — | 50% milk |
| 1.5 | 3.0 | <5 | <5 |
| 1.5 | 2.5 | <5 | <5 |
| 1.5 | 2.0 | <5 | <5 |
| 1.5 | 1.5 | <5 | <5 |
| 1.5 | 1.0 | <5 | <5 |
| 1.5 | 0.5 | <5 | <5 |
| 1.5 | 0.0 | <5 | <5 |
| | 3.0 | <5 | 5 |
| | 2.5 | <5 | <5 |
| | 2.0 | <5 | 170 |
| | 1.5 | <5 | <5 |
| | 1.0 | <5 | 10 |
| | 0.5 | <5 | $3.75 \times 10^6$ |
| | 0.0 | <5 | $5.70 \times 10^7$ |

*Initial viable count: $3.7 \times 10^9$ cfu/ml

TABLE IV

| | | S. aureus (cfu/ml)* | |
|---|---|---|---|
| % benzyl alc | % citrate | — | 50% milk |
| 1.5 | 3.0 | <5 | 20 |
| 1.5 | 2.5 | <5 | 10 |
| 1.5 | 2.0 | <5 | 70 |
| 1.5 | 1.5 | <5 | 330 |
| 1.5 | 1.0 | <5 | $6.45 \times 10^3$ |
| 1.5 | 0.5 | <5 | $4.00 \times 10^5$ |
| 1.5 | 0.0 | <5 | $9.65 \times 10^7$ |
| | 3.0 | <5 | $1.30 \times 10^3$ |
| | 2.5 | <5 | $6.15 \times 10^5$ |
| | 2.0 | <5 | $5.04 \times 10^6$ |
| | 1.5 | <5 | $2.68 \times 10^7$ |
| | 1.0 | <5 | $1.72 \times 10^8$ |
| | 0.5 | <5 | $4.40 \times 10^7$ |
| | 0.0 | 5 | $2.74 \times 10^8$ |

*Initial viable count: $2.35 \times 10^8$ cfu/ml.

EXAMPLE 5

Wipes were formulated with PDF as in Table I except that Arlasolve 200 was substituted for polysorbate 20, nisin concentration was 50 ug/ml, NaCl was 300 mM where present, and citrate was 1% where present. Paper from various sources was used in the various wipes formulations. Nisin stability was monitored by HPLC after storage of the wipe formulations at room temperature. The results are presented in Tables V and VI.

The data confirms that several papers are suitable, including hydroentangled cellulose (HEC), when the formulations contain methionine to prevent degradation of nisin, plus either NaCl or citrate to prevent adsorptive losses of nisin.

TABLE V

| Trial # MA3-16 Paper Product NaCl +/− Met | | | | | | | |
|---|---|---|---|---|---|---|---|
| day 1 | day 6 | day 18 | day 28 | +/− Nisin Concentration ug/ml | | | |
| 1 | Chubbs | + | − | 22.2 | 35.6 | 30.6 | 26.5 |
| 2 | Chubbs | − | − | 45.4 | 46.9 | 43.1 | 43.2 |
| 3 | New Chubbs | + | + | 49.2 | 49.0 | 47.1 | 42.1 |
| 4 | New Chubbs | + | − | 42.1 | 37.4 | 29.7 | 25.2 |
| 5 | New Chubbs | − | + | 52.5 | 53.6 | 50.6 | 44.9 |
| 6 | New Chubbs | − | − | 44.5 | 35.2 | 25.3 | 21.1 |
| 7 | AMBI #546 | + | + | 49.6 | 52.9 | 53.0 | 40.8 |
| 8 | AMBI #546 | + | − | 52.7 | 43.7 | 37.9 | 36.0 |
| 9 | AMBI #546 | − | + | 46.7 | 56.9 | 60.2 | 48.2 |
| 10 | AMBI #546 | − | − | 45.6 | 42.2 | 34.5 | 26.2 |
| 11 | HEC paper | + | + | 50.6 | 53.4 | 56.6 | 46.8 |
| 12 | HEC paper | + | − | 41.5 | 42.5 | 45.1 | 33.9 |
| 13 | HEC paper | − | + | 53.2 | 55.2 | 61.8 | 48.8 |
| 14 | HEC paper | − | − | 44.2 | 40.4 | 38.0 | 29.2 |
| 15 | Scott 1480 | + | + | 49.6 | 56.1 | 61.4 | 51.0 |
| 16 | Scott 1480 | + | − | 43.8 | 44.4 | 43.5 | 33.1 |
| 17 | Scott 1480 | − | + | 53.1 | 56.9 | 60.5 | 49.3 |
| 18 | Scott 1480 | − | − | 43.5 | 38.0 | 27.4 | 22.8 |
| 19 | Scott 129 | + | + | 49.4 | 52.1 | 55.9 | 31.7 |
| 20 | Scott 129 | + | − | 46.0 | 44.9 | 45.2 | 35.5 |
| 21 | Scott 129 | − | + | 44.1 | 41.7 | 29.1 | 26.7 |
| 22 | Scott 129 | | | | | | |
| Stock Solution | | − | − | 35.9 | 29.3 | 16.5 | 16.1 |
| 23 | MA3-15-1 | + | + | 52.1 | 49.3 | 48.7 | 39.0 |
| 24 | MA3-15-2 | + | − | 45.6 | 37.6 | 30.8 | 26.0 |
| 25 | MA3-15-3 | − | + | 55.1 | 52.3 | 48.6 | 39.6 |
| 26 | MA3-15-4 | − | − | 45.6 | 36.3 | 25.6 | 25.5 |

TABLE VI

| Trial # MA3-29 | Paper Product | Citrate +/− | Methionine +/− | Nisin Concentration | | |
|---|---|---|---|---|---|---|
| | | | | day 0 | day 14 | day 28 |
| 1 | New Chubbs | + | + | 38.5 | 31.4 | 42.0 |
| 2 | New Chubbs | + | − | 21.0 | 17.8 | 23.6 |
| 3 | New Chubbs | − | + | 34.6 | 26.3 | 21.8 |
| 4 | New Chubbs | − | − | 13.5 | 28.0 | 27.3 |
| 5 | AMBI #546 | + | + | 42.1 | 39.2 | 48.2 |
| 6 | AMBI #546 | + | − | 24.0 | 20.8 | 30.2 |
| 7 | AMBI #546 | − | + | 34.9 | 7.4 | 7.6 |
| 8 | AMBI #546 | − | − | 13.5 | 3.8 | 6.3 |
| 9 | HEC* paper | + | + | 40.0 | 38.2 | 46.9 |
| 10 | HEC paper | + | − | 22.0 | 24.9 | 37.9 |
| 11 | HEC paper | − | + | 33.3 | 17.8 | 15.9 |
| 12 | HEC paper | − | − | 16.3 | 4.8 | 11.3 |
| 13 | MA3-29-1 STOCK | + | + | 40.8 | 37.1 | 41.9 |
| 14 | MA3-29-2 STOCK | + | − | 22.6 | 17.2 | 23.0 |
| 15 | MA3-29-3 STOCK | − | + | 39.6 | 33.5 | 39.9 |

TABLE VI-continued

| Trial # | Paper | Citrate | Methionine | Nisin Concentration | | |
|---|---|---|---|---|---|---|
| MA3-29 | Product | +/− | +/− | day 0 | day 14 | day 28 |
| 16 | MA3-29-4 STOCK | − | − | 19.3 | 30.2 | 36.5 |

*Hydroentangled cellulose paper

EXAMPLE 6

This study was performed to determine the amount of liquid sufficient to wet a towelette for use as a Wipe product. Measured areas of each paper sample were weighed, then wet with PDF so as to be thoroughly moist without being dripping wet, and weighed again to determine the amount of formulation required for this condition. The results are seen in Table VII.

TABLE VII

| Paper | Total Area | Weight of Paper | Weight of Wet Paper | Liquid Added | ml liquid /cm² paper |
|---|---|---|---|---|---|
| New Chubbs | 344.0 cm² | 1.92 g | 8.20 g | 6.4 ml | .019 |
| #546 | 310.6 cm² | 1.17 g | 3.60 g | 2.3 ml | .007 |
| #565 hydroentangled cellulose | 288.5 cm² | 1.13 g | 4.50 g | 3.3 ml | .011 |

EXAMPLE 7

Formulated wipes prepared as shown in Table I but with 300 mM NaCl were evaluated for germicidal performance on live cow teat skin according to the following protocol A.

Protocol A

Ten cows were prepped and cleaned for protocol A. This involved removing the hair from the bottom side of the udders and a series of washings. The cows' teats were washed with Theratec (0.5% iodophor), thoroughly rinsed with water, and then wiped down with alcohol swabs. Collection cups were labelled and placed beside each cow, four per cow. Each teat dipped to 15 mm with a suspension of bacteria at approximately $10^8$ cells/ml. After ten minutes, the teat was dipped with the appropriate test solution to a depth of 30 mm or wiped with one towelette. The wiping action consisted of grabbing the teat at its base, pulling down and off, turning the hand 90- and grabbing the teat at its base once again, pulling down and off. After one minute, surviving cells were harvested using a syringe.filled with 10 ml of quenching solution to neutralize the action of nisin and to collect bacteria from the surface of the teat into a collection cup. Collection cups were immediately capped and placed on ice in a cooler. Approximately one hour later, the 80 samples were diluted and plated in duplicate on blood agar plates. Plates were incubated at 37° C. for 24–48 hours. Colony forming units (cfu) were scored and reductions in cfu were calculated relative to cfu recovered from the control teats. All four teats were tested on each cow, and a total of 20 cows were tested. The two hind teats were the control teats, that is they were dipped in water. The two front teal-s were tested with the one of the germicidal products.

Results, expressed as log reduction in cfu, for S. aureus, are presented in Table VIII. The log reduction value per cow was calculated by subtracting the mean log cfu of the two test (front) teats from the mean log cfu of the two control (hind) teats. The Total Mean Log Reduction for the five cows in each test condition is also reported in Table VIII.

The PDF wipes performed comparably to the PDF dip. The action of wiping alone, with a water wipe, yielded a 1.7-log reduction.

TABLE VIII

| COW | Theratec (0.5% iodophor) | COW | PDF (25 ug/ml nisin) | COW | PDF Wipes | COW | Water Wipes |
|---|---|---|---|---|---|---|---|
| #1 | 0.5 | #6 | 3.3 | #11 | 3.6 | #16 | 1.7 |
| #2 | 0.7 | #7 | 3.2 | #12 | 2.7 | #17 | 1.9 |
| #3 | 0.4 | #8 | 2.7 | #13 | 1.9 | #18 | 1.8 |
| #4 | 0.5 | #9 | 4.2 | #14 | 2.4 | #19 | 1.6 |
| #5 | 0.8 | #10 | 1.6 | #15 | 2.2 | #20 | 1.4 |
| TOTAL MEAN LOG RED | 0.6 | TOTAL MEAN LOG RED | 3.0 | TOTAL MEAN LOG RED | 2.6 | TOTAL MEAN LOG RED | 1.7 |

EXAMPLE 8

Wipes formulation (PDF) was prepared as described in Table I except that 1% Arlasolve 200 was used in place of polysorbate 20 and 1% citrate was used in place of NaCl, and nisin was at 50 ug/ml. Where present, 1-propanol was at 20%. The test formulations, #1 with and #2 without 1-propanol, were evaluated for germicidal performance toward S. aureus on live cow teat skin according to protocol A (above), and compared with the performance of Theratec (0.5% iodophor) and PDF teat dip.

The results are presented in Table IX and demonstrate that both wipes formulations performed comparably against S. aureus, and were equivalent to the performance of the 0.5% iodophor.

TABLE IX

| COW | WIPES #1 50 ug/ml nisin | COW | WIPES #2 50 ug/ml nisin | COW | Theratec 0.5% Iodophor | COW | PDF 25 ug/ml nisin |
|---|---|---|---|---|---|---|---|
| #1 | 1.9 | #6 | 2.4 | #11 | 2.4 | #16 | 4.3 |
| #2 | 3.4 | #7 | 2.4 | #12 | 3.1 | #17 | 2.3 |
| #3 | 3.4 | #8 | 3.9 | #13 | 1.7 | #18 | 2.5 |
| #4 | 2.3 | #9 | 2.6 | #14 | 2.2 | #19 | 4.7 |
| #5 | 2.9 | #10 | 3.1 | #15 | 2.7 | #20 | 4.7 |
| TOTAL MEAN LOG RED | 2.8 | TOTAL MEAN LOG RED | 2.9 | TOTAL MEAN LOG RED | 2.4 | TOTAL MEAN LOG RED | 3.7 |

EXAMPLE 9

Wipes formulation (PDF) was prepared as described in example 8 and used to prepare moist paper wipes with liquid content at 3 g, 5 g, and 7 g per wipe (6 in×6.75 in). These wipes were evaluated for germicidal activity against *E. coli* on live cow teat skin according to protocol A (above), and compared with the performance of Theratec (0.5% iodophor).

The results are presented in Table X and demonstrate that 7 g liquid / wipe provide germicidal activity superior to that of the wipes with lower liquid loading.

TABLE X

| date | formulation | target | log reduction treatment | positive control |
|---|---|---|---|---|
| 2/2/95 | PDF wipes, 3 g/wipe | E. coli | 2.2 | 3.2 |
|  | PDF wipes, 5 g/wipe |  | 3.4 |  |
|  | PDF wipes, 7 g/wipe |  | 3.7 |  |

EXAMPLE 10

Wipes formulation (PDF) was prepared as described in example 8 and used to prepare moist paper wipes. These wipes were evaluated for germicidal activity against a range of organisms on live cow teat skin according to protocol A (above), and compared with the performance of several teat dips as positive controls.

The results are presented in Table XI and demonstrate that the PDF formulated wipes have effective germicidal activity on cows' teats against the major pathogenic organisms implicated in mastitis infections.

TABLE XI

| cow teats (n=) | target | log reduction treatment | positive control |
|---|---|---|---|
| 10 | S. aureus | 2.5 | 0.2* |
| 10 | S. agalactiae | 4.3 | 0.7* |
| 10 | S. uberis | 3.0 | 3.3* |
| 10 | Klebsiella | 2.6 | 3.2* |
| 10 | E. coli | 2.3 |  |
| 10 | S. aureus | 3.4 |  |
| 10 | S. uberis | 2.8 | 2.5$ |
| 10 | K. | 3.1 | 4.1$ |

TABLE XI-continued

| cow teats (n=) | target | log reduction treatment | positive control |
|---|---|---|---|
|  | pneumoniae |  |  |
| 10 | S. aureus | 3.4 | 3.0$ |
| 10 | E. coli | 2.0 | 4.0$ |

*Consept Pre + Post Teat Dip
$Teat Guard 1% iodophor Teat Dip

EXAMPLE 11

Formulated wipes prepared as shown in Table I but with 12% 1-propanol, 3 mM EDTA, and 5 mM citrate, were used in an Experimental Challenge trial following the standard protocol of the NMC. A dairy herd of 160 cows at Cornell University Veterinary College was used to test the efficacy of the PDF wipes in the field. The four treatment conditions are summarized in Table XII, there were 40 cows in each treatment group. To create extreme infectious conditions promoting the likelihood of mastitis infections each cow's teats were dipped in a suspension of *S. aureus* and *S. agalactiae* ($10^8$ cfu/ml for each organism) immediately after the afternoon milking Monday to Friday. The bacterial challenge was followed immediately by the postmilking sanitization appropriate for that group.

The data presented in Table XII show that the PDF wipes used as a post-milking treatment, or as a premilking treatment in conjunction with post dipping with Consept teat dip, reduce the incidence of mastitis infections comparable to the effect of Theratec (0.5% iodophor) teat dip.

TABLE XII

| group | premilking treatment | postmilking treatment | mastitis infections at 2 weeks |
|---|---|---|---|
| A – ve control | wash with water-soaked paper towel dry with separate paper towel | none | 13 |
| B + ve control | wash with water -soaked paper towel dip with Theratec 0.5% iodophor dry with separate paper towel | dip with Theratec 0.5% iodophor | |
| C | clean and sanitize with PDF Wipes | dip with nisin-based Consept teat dip | 6 |
| D | wash with water-soaked paper towel dry with separate paper towel | sanitize with PDF Wipe | 7 |

We claim:

1. A moist paper or fabric wipe containing a liquid formulation comprising a suitable amount of a bacteriocin, a chelating agent, a stabilizer, a surfactant, a salt and an alcohol drying agent.

2. A wipe according to claim 1 wherein the bacteriocin is a lanthocin; the chelating agent is selected from one or more of an alkydiamine tetraacetate, EGTA and citrate; the stabilizer is a thioether compound; the surfactant is a nonionic surfactant, a cationic surfactant, a monoglyceride or a fatty acid; and the salt is NaCl.

3. A wipe according to claim 2 wherein the lanthocin is nisin, the chelating agent is EDTA, the stabilizer is methionine, the surfactant is polysorbate 20 and the drying agent is 1-propanol.

4. A wipe according to claim 3, wherein the chelating agent comprises EDTA and citrate in combination.

5. A wipe according to claim 3 wherein the concentration of nisin is in the range of 25 to 500 ug/ml and the concentration of NaCl is in the range of 10 to 300 mM.

6. A wipe according to claim 3 wherein the concentration of EDTA is in the range of 0.1 to 10 mM.

7. A wipe according to claim 4 wherein the concentration of EDTA is in the range of 0.1 to 10 mM and the concentration of citrate is in the range of 1 to 30 mM.

8. A wipe according to claim 3 wherein the concentration of methionine is in the range of 1 to 10 mM.

9. A wipe according to claim 3 wherein the concentration of polysorbate 20 is in the range of 0.1 to 3%.

10. A wipe according to claim 3 wherein the concentration of 1-propanol is in the range of 10 to 20%.

11. A wipe according to claim 1 wherein the formulation further comprises a conditioner and a thickener.

12. A wipe according to any one of claims 1–4, wherein the formulation further comprises chlorhexidine.

13. A wipe according to any one of claims 1–4 wherein the paper wipe is of a non-woven material.

14. A one-step method for disinfecting and drying a cow teat prior to milking which comprises wiping the teat with a wipe according to any one of claims 1–4.

15. A one-step method for disinfecting and drying a cow teat after milking which comprises wiping the teat with a wipe according to any one of claims 1–4.

16. A one-step method for disinfecting and drying a skin surface which comprises wiping the skin surface with a wipe according to any one of claims 1–4.

17. A one-step method for cleansing a skin surface which comprises wiping the skin surface with a wipe according to any one of claims 1–4.

18. A one-step method for disinfecting and drying a food contact surface which comprises wiping the food contact surface with a wipe according to any one of claims 1–4.

19. A method for reducing the incidence of mastitis infection in dairy animals, which comprises wiping the animals' teats after milking with a wipe according to any one of claims 1–4.

20. A method for reducing the incidence of mastitis infection in dairy animals, which comprises pre-milking wiping of the animals' teats with a wipe according to any one of claims 1–4 in conjunction with post-dipping with Consept teat dip.

* * * * *